(12) United States Patent
Kim et al.

(10) Patent No.: US 12,121,283 B2
(45) Date of Patent: Oct. 22, 2024

(54) ULTRASONIC MEDICAL INSTRUMENT HAVING VARIABLE FOCUSING DEPTH OF ULTRASONIC WAVE GENERATING UNIT

(71) Applicant: JEISYS MEDICAL INC., Seoul (KR)

(72) Inventors: Min Young Kim, Seoul (KR); Kyun Tae Kim, Seoul (KR); Ki Ho Jeong, Seoul (KR); Won Ju Yi, Seoul (KR); Dong Hwan Kang, Seoul (KR)

(73) Assignee: Jeisys Medical Inc., Seoul (KR)

( * ) Notice: Subject to any disclaimer, the term of this patent is extended or adjusted under 35 U.S.C. 154(b) by 514 days.

(21) Appl. No.: 17/474,377

(22) Filed: Sep. 14, 2021

(65) Prior Publication Data

US 2022/0079650 A1 Mar. 17, 2022

(30) Foreign Application Priority Data

Sep. 17, 2020 (KR) ........................ 10-2020-0119733

(51) Int. Cl.
*A61B 18/12* (2006.01)
*A61B 18/00* (2006.01)

(52) U.S. Cl.
CPC .... *A61B 18/12* (2013.01); *A61B 2018/00464* (2013.01); *A61B 2018/00738* (2013.01); *A61B 2018/00952* (2013.01); *A61B 2018/00994* (2013.01)

(58) Field of Classification Search
CPC .......... A61B 18/12; A61B 2018/00738; A61B 2018/00636; A61B 2018/00952; A61N 7/02; A61N 2007/0082; A61N 2007/0091
See application file for complete search history.

(56) References Cited

U.S. PATENT DOCUMENTS

| | | | | |
|---|---|---|---|---|
| 3,583,540 A | * | 6/1971 | Bernard | B41J 13/32 400/636 |
| 4,541,434 A | * | 9/1985 | Okado | G10K 11/357 73/633 |
| 4,593,820 A | * | 6/1986 | Antonie | G01R 31/2893 901/44 |
| 4,637,256 A | * | 1/1987 | Sugiyama | G10K 11/352 73/621 |
| 5,107,113 A | * | 4/1992 | Robinson | G01Q 30/06 250/307 |

(Continued)

FOREIGN PATENT DOCUMENTS

| | | |
|---|---|---|
| JP | 2020-505116 A | 2/2020 |
| KR | 10-20120040909 | 4/2012 |

(Continued)

OTHER PUBLICATIONS

European Patent Office, Extended European Search Report issued in European Patent Application No. 21195712.1 (May 24, 2022).

(Continued)

*Primary Examiner* — Oommen Jacob
(74) *Attorney, Agent, or Firm* — Leydig, Voit & Mayer, Ltd.

(57) ABSTRACT

Embodiments of the inventive concept provide an ultrasonic medical instrument moving horizontally by adjusting a depth wise location of an ultrasonic wave generating unit while not influencing an internal volume of a cartridge and variously setting focusing depths of ultrasonic waves in skin.

20 Claims, 10 Drawing Sheets

(56) References Cited

U.S. PATENT DOCUMENTS

| | | | | |
|---|---|---|---|---|
| 5,466,935 A * | 11/1995 | Ray | ........................ | G01Q 30/04 850/28 |
| 5,685,232 A * | 11/1997 | Inoue | .................... | A47B 85/00 108/22 |
| 6,102,866 A * | 8/2000 | Nields | .................... | A61B 90/17 600/407 |
| 6,190,323 B1 * | 2/2001 | Dias | ..................... | A61B 8/4461 600/446 |
| 6,380,661 B1 * | 4/2002 | Henderson | ............. | H02N 2/023 310/323.02 |
| 6,846,289 B2 * | 1/2005 | Besson | ................ | A61B 8/0825 600/437 |
| 7,146,741 B2 * | 12/2006 | Butter | ................... | G01B 11/007 33/561 |
| 8,510,883 B2 * | 8/2013 | Eilers | .................... | A61G 13/121 5/655.4 |
| 8,926,533 B2 * | 1/2015 | Bockenstedt | ........ | G10K 11/352 601/2 |
| 10,537,304 B2 * | 1/2020 | Barthe | .................... | A61B 8/465 |
| 10,646,201 B2 * | 5/2020 | Cox | ...................... | A61B 8/0841 |
| 11,351,401 B2 * | 6/2022 | Emery | ................... | G10K 11/30 |
| 2001/0016680 A1 * | 8/2001 | Minami | ............... | G02B 23/2438 600/168 |
| 2002/0175149 A1 * | 11/2002 | Gruber | ................... | G02F 1/3525 219/121.6 |
| 2004/0129873 A1 * | 7/2004 | Lindsay | ................. | B82Y 35/00 250/234 |
| 2007/0292119 A1 * | 12/2007 | Lee | ......................... | H04N 23/68 348/E5.046 |
| 2008/0097214 A1 * | 4/2008 | Meyers | ................. | A61B 8/4461 600/459 |
| 2008/0281202 A1 * | 11/2008 | Fraser | ................. | A61B 17/1355 601/3 |
| 2009/0171252 A1 * | 7/2009 | Bockenstedt | ........ | G10K 11/352 601/2 |
| 2014/0155747 A1 * | 6/2014 | Bennett | ................. | H04R 31/00 600/439 |
| 2015/0133788 A1 * | 5/2015 | Mauldin, Jr. | ........... | A61B 8/523 600/444 |
| 2015/0265243 A1 * | 9/2015 | Kelly | .................... | A61B 8/4218 600/443 |
| 2016/0001097 A1 | 1/2016 | Cho et al. | | |
| 2017/0303895 A1 * | 10/2017 | Park | ........................ | A61N 7/02 |
| 2017/0354395 A1 | 12/2017 | Lupotti et al. | | |
| 2019/0290939 A1 * | 9/2019 | Watson | .................. | A61B 90/37 |
| 2020/0061394 A1 | 2/2020 | Yoo | | |

FOREIGN PATENT DOCUMENTS

| | | |
|---|---|---|
| KR | 10-2013-0106361 A | 9/2013 |
| KR | 10-1429002 | 8/2014 |
| KR | 10-20180015095 | 2/2018 |
| KR | 10-1893584 B | 8/2018 |
| KR | 102008869 B1 | 8/2019 |
| WO | WO 2014129732 A1 | 8/2014 |

OTHER PUBLICATIONS

Korean Intellectual Patent Office Notice of Office Action issued in Korean 10-2020-0119733 (Sep. 26, 2022).
Japensese Patent Office Notice of Reasons for Refusal in Japanese Application No. 2023-063520 (Apr. 16, 2024).

* cited by examiner

150

ULTRASONIC MEDICAL INSTRUMENT HAVING VARIABLE FOCUSING DEPTH OF ULTRASONIC WAVE GENERATING UNIT

CROSS-REFERENCE TO RELATED APPLICATIONS

A claim for priority under 35 U.S.C. § 119 is made to Korean Patent Application No. 10-2020-0119733 filed on Sep. 17, 2020 in the Korean Intellectual Property Office, the entire contents of which are hereby incorporated by reference.

BACKGROUND

The inventive concept relates to an ultrasonic medical instrument, and more particularly, to an ultrasonic medical instrument having a handpiece and a cartridge for an ultrasonic medical instrument that is attached to the handpiece to generate ultrasonic waves.

A fatty tissue layer is present under the dermis and the epidermis of human skin. Cellulite may be easily generated in a subcutaneous fat layer and subcutaneous fat may be organized in a specific chamber surrounded by strands of connected tissues, and thus the subcutaneous fat layers are unique as compared with the other fat layers. Excessive fatty tissues may be the cause of obesity, cellulite, deflected skin, and wrinkles.

The subcutaneous fat layers that occupy most of the fatty tissues are divided into thin fat layers and deep fat layers. The deep fat layers are present between subcutaneous fascia and muscle fascia in the abdomen, waist, hips, and thighs, and form deep fat divisions. The deep fat layers tend to be clearly accumulated in local areas. The volumes of the local fat accumulations generated due to aging increase in a limited space due to slimness or lack in fibrous partition walls. Accordingly, they tend to swell at portions below the waist.

Because excessive local concentration of fats expands skin convexly and contours of the skin that are not preferable remove fat layers that are abundant in lipid, the shape of the outer layer of the skin may thus be improved.

In recent years, a procedure using ultrasonic waves in a noninvasive method of reducing subcutaneous fat layers or fatty tissues has been widely known.

The ultrasonic waves refer to waves having frequencies of 20 kHz or more, and which are variously utilized in the diagnosis and treatment of affected parts in both the medical and skin cosmetic fields.

In particular, unlike a laser and radio frequency (RF) equipment, high-intensity focused ultrasound (HIFU) that is obtained by focusing ultrasonic waves at high intensity cause a rapid rise in temperature in a surgical portion by concentrating energy on a noninvasively selected portion while not damaging a surface of the skin, that is, by focusing emitted ultrasonic waves at a focus that is a specific point to generate heat. Through the heating function, coagulation necrosis is induced to fat cells while leaving no side-effects at various affected parts while performing a surgical procedure.

Meanwhile, in the treatment using ultrasonic waves, it is most effective to adjust the focal locations of the ultrasonic waves when portions of skin to be treated are changed. That is, it is necessary to adjust the focusing location of a transducer such that the focal locations of the ultrasonic waves irradiated by the transducer correspond to a subcutaneous fat layer that is a treated portion.

However, in a conventional ultrasonic wave generating device, because a location of the transducer that generates ultrasonic waves is fixed, in a Z axial direction, that is, because focal locations of the ultrasonic waves irradiated by the transducer is fixed, it is impossible to adjust the focusing depths of the ultrasonic waves according a skin portion to be treated. Accordingly, a plurality of cartridges having focusing depths of ultrasonic waves according to the skin portion to be treated have to be provided.

Accordingly, the applicant(s) developed an ultrasonic medical instrument that embeds an ultrasonic wave generating unit (that is, a transducer) in a cartridge that is attached to a handpiece to be replaceable, may move focal locations of ultrasonic waves irradiated by the ultrasonic wave generating unit embedded in the cartridge to a uniform depth in skin and may variably adjust focusing depths of the ultrasonic waves.

RELATED TECHNICAL DOCUMENT

Patent Document (Patent Document 1) Korean Patent Application Publication No. 10-2013-0106361 (entitled "HIFU Applicator" published on Sep. 27, 2013)

SUMMARY

Embodiments of the inventive concept provide an ultrasonic medical instrument moving horizontally by adjusting a depth wise location of an ultrasonic wave generating unit while not influencing an internal volume of a cartridge and variously setting focusing depths of ultrasonic waves in skin.

According to an embodiment, a cartridge for an ultrasonic medical instrument includes a cartridge housing detachably mounted on a handpiece, a first movement unit accommodated in the cartridge housing, and configured such that a first movable body reciprocates in a first axial direction, a second movement unit coupled to one side of the first movable body, of which a location in the first axial direction is changed by the first movement unit, and configured such that a second movable body reciprocates in a second axial direction that is perpendicular to the first axial direction, and an ultrasonic wave generating unit coupled to the second movable body, and that generates high-intensity focused ultrasound having a specific focusing distance, wherein a disposition location of the second movement unit in the first axial direction in the cartridge is set according to a location movement of the first movable body, the second movement unit includes a piezoelectric motor driven based on an electrical signal by a power source, and the first movement unit and the second movement unit are controlled by a controller included in the handpiece or a body, to which the handpiece is connected.

Furthermore, the first movement unit may be coupled to the handpiece, and may change the location of the first movable body in first axial direction with power provided by a driving unit in the handpiece.

Furthermore, the driving unit may change the disposition location of the first movable body in the first axial direction with the first movement unit and may change a location of the second movable body in the second axial direction at the same time when a treatment is performed by outputting ultrasonic waves.

Furthermore, the electrical signal may be an RF signal.

Furthermore, the cartridge may further include a movement module location measuring unit that calculates a location of the ultrasonic wave generating unit in the second axial direction.

Furthermore, the cartridge may further include a movement module location measuring unit that calculates a disposition location of the ultrasonic wave generating unit in the second axial direction, and the movement module location measuring unit may measure a distance to the ultrasonic wave generating unit that is parallel to the first axial direction.

Furthermore, the cartridge may further include a movement module location measuring unit that calculates a disposition location of the ultrasonic wave generating unit in the second axial direction, the movement module location measuring unit may be installed to be spaced apart from the second movement body along the second axial direction, a relative distance from the movement module location measuring unit to the second movement body may be measured by outputting sensing light to the second movement body along the second axial direction and sensing the light in a location measuring unit installed in the second movement body, and a location of the ultrasonic wave generating unit in the second axial direction may be calculated based on the measured distance.

Furthermore, the second movable body may include a through-hole in a center thereof, and a movement shaft of the second movement unit may pass through the through-hole to be coupled thereto.

Furthermore, the piezoelectric motor may be a piezoelectric rotary motor coupled to the first movement body, the piezoelectric rotary motor may have a driving shaft disposed along the second axial direction, and the second movement body may be installed to be reciprocally movable in the second axial direction through rotation of the driving shaft.

Furthermore, the first movable body may have a guide unit that supports the second movable body to prevent rotation of the second movable body, a spiral screw may be formed in the driving shaft in the second axial direction, a screw hole screw-coupled to the screw may be formed in the second movable body, and as the second movable body is moved along the screw in the second axial direction when the driving shaft is rotated, the locations of the second movable body and the ultrasonic wave generating unit in the second axial direction may be changed.

Furthermore, the cartridge may further include an ultrasonic wave generating unit location measuring unit that detects the location of the ultrasonic wave generating unit in the second axial direction.

Furthermore, the ultrasonic wave generating unit location measuring unit may be installed to be spaced apart from the second movement body along the first axial direction, a relative distance from the ultrasonic wave generating unit location measuring unit to the second movement body may be measured by outputting sensing light to the second movement body and sensing reflection light reflected by the second movement body, and a location of the ultrasonic wave generating unit in the second axial direction may be calculated based on the measured distance.

Furthermore, the cartridge may further include a reflection plate that improves a reflectivity of the sensing light at a point, at which the sensing light is input from the second movable body.

According to an embodiment, an ultrasonic medical instrument includes the cartridge, and a handpiece, on which the cartridge is detachably mounted, and that transmits an RF signal and power for driving of the cartridge in a first axial direction to the cartridge.

Meanwhile, the piezoelectric motor is small and light as compared with the conventionally used electric motor, and may not influence the first axis movement. The conventional electric motor is large and heavy to apply a load to the shaft during the first axis movement, and the axial movement is interfered by a plurality of signals and a plurality of power cables so that the axial movement is not free.

Furthermore, the conventional electric motor is weak to water but a waterproof performance of the piezoelectric motor is high so that it is easy to use the piezoelectric motor in the ultrasonic medical cartridge.

The piezoelectric motor may be a piezoelectric linear motor or a piezoelectric rotary motor, and preferably, may be a piezoelectric rotary motor.

In the piezoelectric linear motor, the ultrasonic wave generating unit is influenced by the gravitational force so that the location of the ultrasonic wave generating unit may be changed and deviate from a desired treatment location because the ultrasonic wave generating unit is fixed only by the frictional force of the movable shaft, but in the piezoelectric rotary motor, the ultrasonic wave generating unit is not influenced by the gravitational force, a depth may be precisely adjusted, and the ultrasonic wave generating unit may be operated without being influenced by the first axis movement and the second axis movement.

The ultrasonic medical instrument according to the embodiment of the present disclosure may include the above-described cartridge, and a handpiece to which the cartridge is detachably mounted, and that transmits an RF signal and power for driving in a first axial direction to the cartridge.

According to the inventive concept, focal locations of ultrasonic waves of the ultrasonic wave generating unit may be moved into a uniform depth in skin on a plane and focal depths of the ultrasonic waves may also be variously adjusted.

Furthermore, when the piezoelectric motor is used to move the ultrasonic wave generating unit in a depth direction, the location of the ultrasonic wave generating unit may be changed while a space for de-airing liquid in the interior of the cartridge is not influenced. Through this, the cartridge structure may be manufactured more simply and the location of the ultrasonic wave generating unit in the interior of the cartridge may be electrically controlled whereby the focusing depth may be adjusted more conveniently by the user.

DETAILED DESCRIPTION

Figure 1:
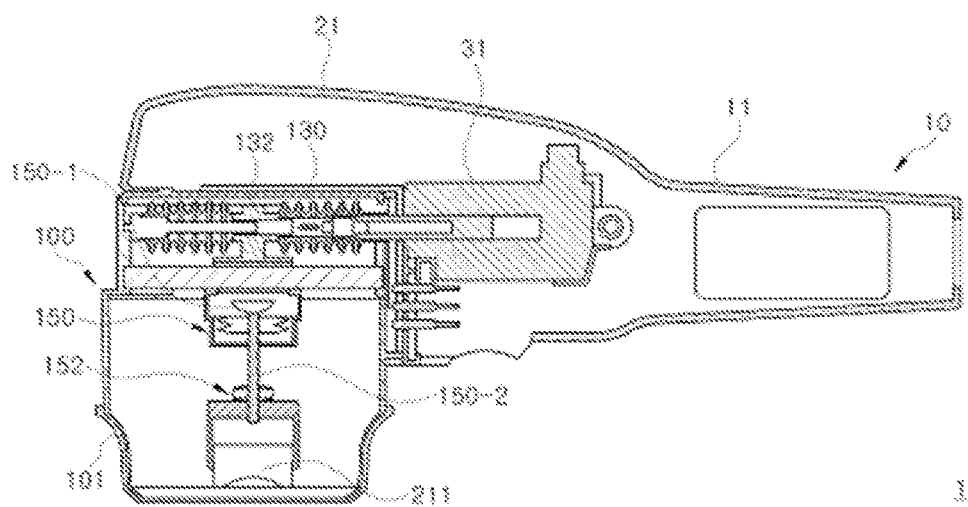
FIG. 1 is a cross-sectional view of an ultrasonic medical instrument that adjusts a depth with a piezoelectric motor according to an embodiment of the inventive concept.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals denote the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

Hereinafter, the inventive concept will be described in detail with reference to the accompanying drawings.

FIG. 1 is a cross-sectional view of an ultrasonic medical instrument that adjusts a depth with a piezoelectric motor according to an embodiment of the inventive concept.

Figure 2:
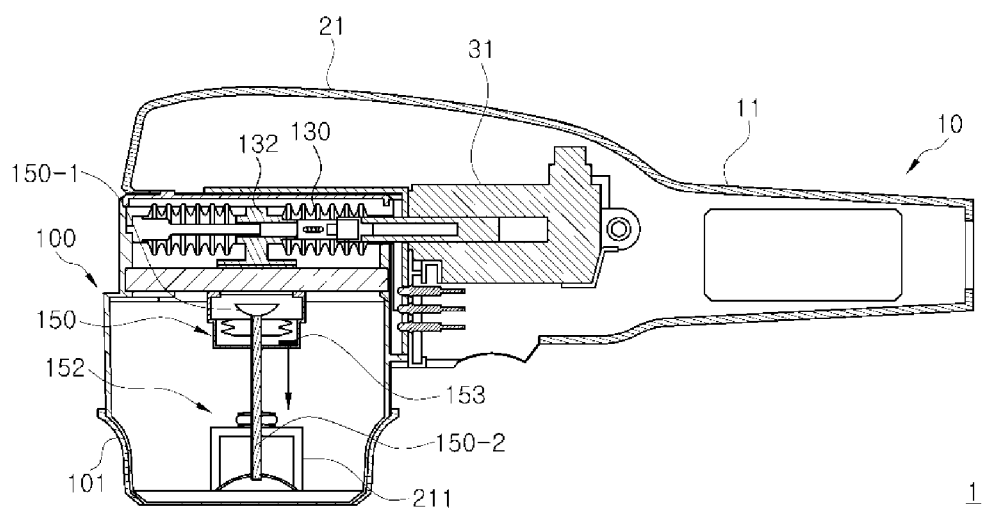
FIG. 2 is a cross-sectional view of an ultrasonic medical instrument further including a distance measuring sensor measuring a location of an ultrasonic wave generating unit according to an embodiment of the inventive concept.

FIG. 2 is a cross-sectional view of an ultrasonic medical instrument further including a distance measuring sensor measuring a location of an ultrasonic wave generating unit according to an embodiment of the inventive concept.

Figure 3:
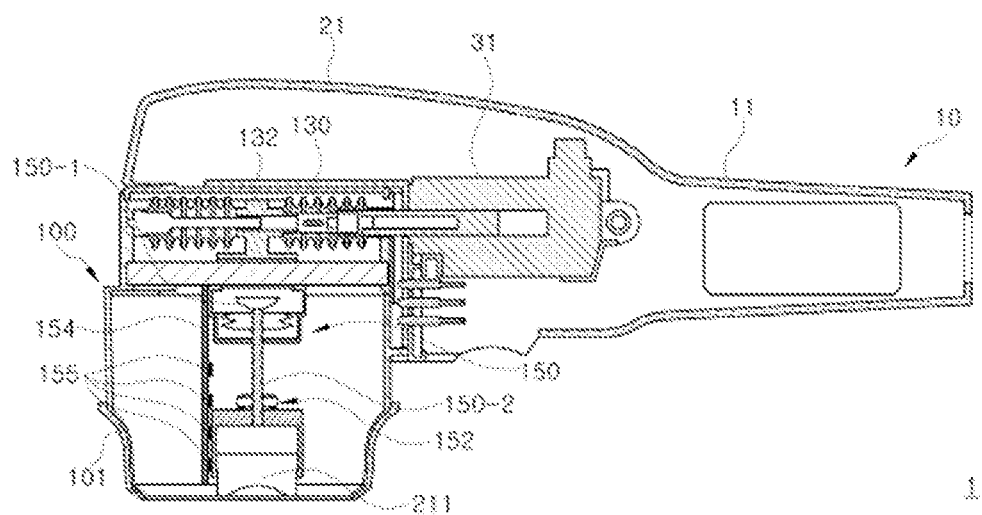
FIG. 3 is a cross-sectional view of an ultrasonic medical instrument including a Hall sensor measuring a location of an ultrasonic wave generating unit, to which a magnet is coupled, according to an embodiment of the inventive concept.

FIG. 3 is a cross-sectional view of an ultrasonic medical instrument including a Hall sensor measuring a location of an ultrasonic wave generating unit, to which a magnet is coupled, according to an embodiment of the inventive concept.

Figure 4:
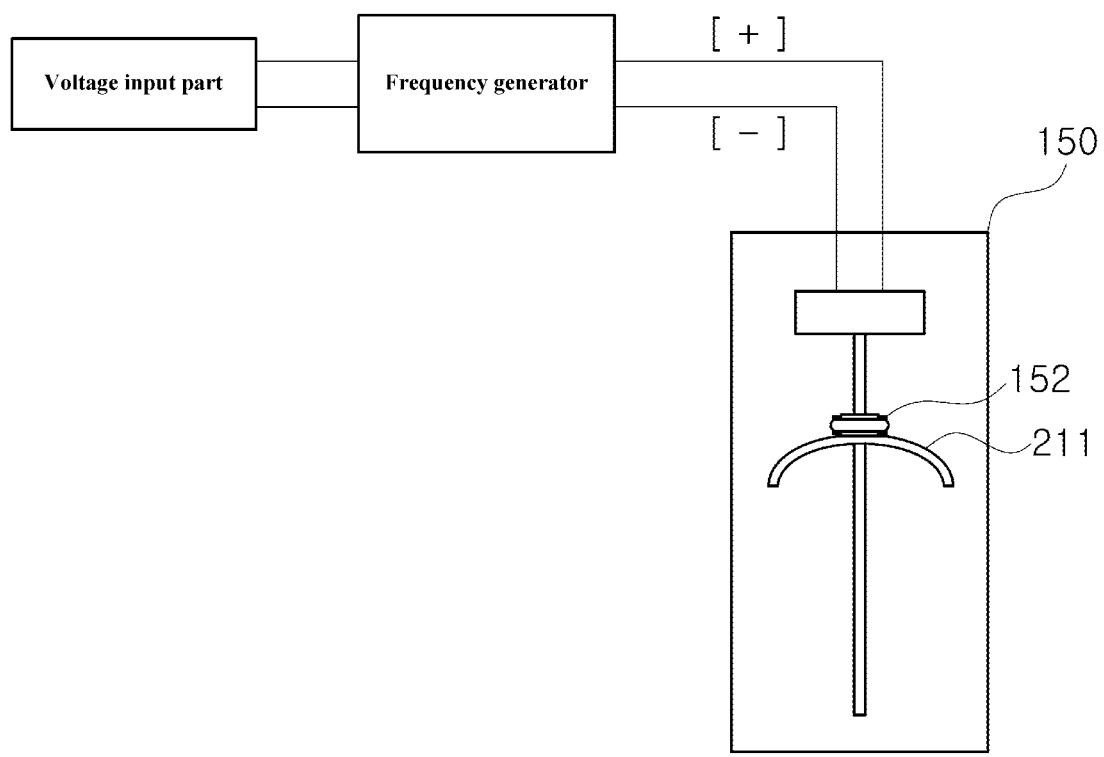
FIG. 4 is an electrical connection diagram of a piezoelectric motor moving an ultrasonic wave generating unit of the inventive concept.

FIG. 4 is an electrical connection diagram of a piezoelectric motor moving an ultrasonic wave generating unit of the inventive concept.

Figure 5:
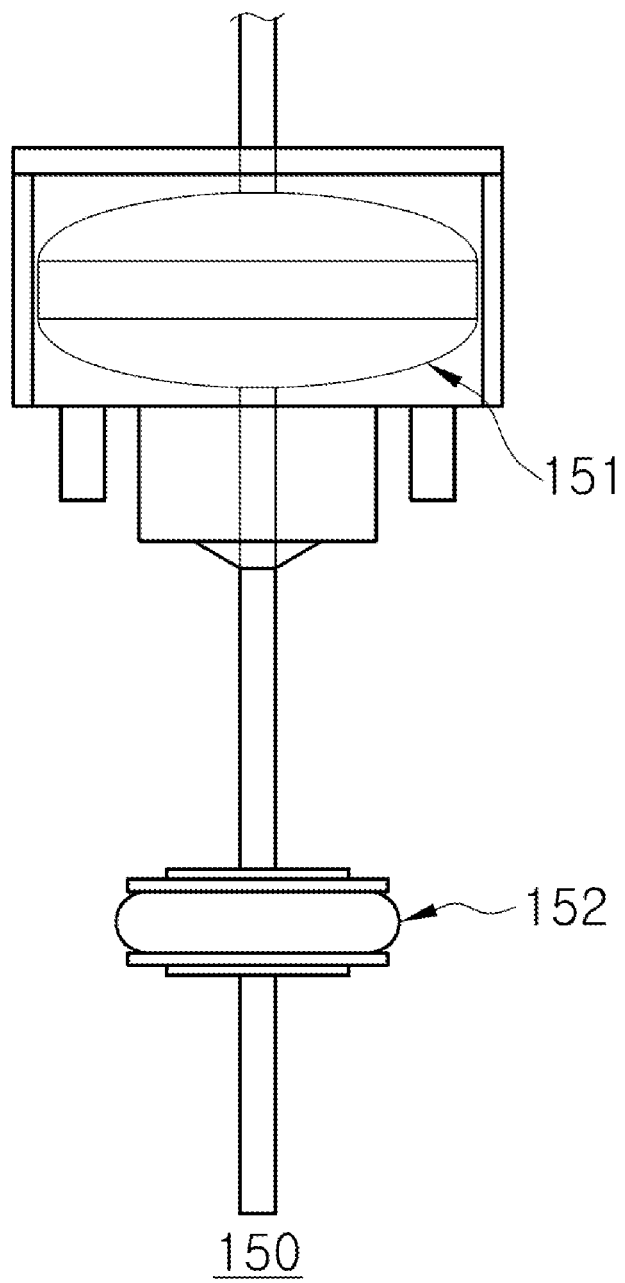
FIG. 5 is an exemplary view of a piezoelectric motor included in embodiments of the inventive concept.

FIG. 5 is an exemplary view of a piezoelectric motor included in embodiments of the inventive concept.

Referring to FIGS. 1 to 3, an ultrasonic medical instrument 1 includes a handpiece 10 and a cartridge 100 for an ultrasonic medical instrument.

The handpiece 10 includes a knob 11 with a rod shape having a specific length to be gripped by a hand, and a head 21 protruding from one end of the knob 11 and on which the cartridge 100 for an ultrasonic medical instrument is detachably mounted.

In representing directions in the inventive concept, a first axial direction is defined by a lengthwise direction of the handpiece 10 and the X axial direction, and a second axial direction that is perpendicular to the first axial direction is defined by the Z axial direction, and an upward/downward direction and a depth direction.

A driving actuator 31 for moving a first movement unit 130 of the cartridge 100 for an ultrasonic medical instrument, which will be described below, in the first axial direction is accommodated in the knob 11.

In detail, a driving unit may include a first driving unit that provides driving for movement of a first movable body 132, which will be described below, in the first axial direction, and a second driving unit that provides driving for movement of a second movable body 152, which will be described below, in the second axial direction.

The first driving unit may be the driving actuator 31 or a motor that may move the first movable body 132 in the first axial direction, but is not specifically limited thereto.

The second driving unit may be an RF generating module (not illustrated) that provides an RF signal to a piezoelectric motor moving the second movable body 152, which will be described below, in the second axial direction, but is not specifically limited thereto.

Furthermore, a controller (not illustrated) for controlling locations of the driving actuator 31 and an ultrasonic wave generating unit 211, which will be described below, (that is, a location of a transducer) is accommodated in the knob 11.

When a configuration that requires an electrical control is added in an interior of the cartridge 100, the controller also may control the added configuration.

An attachment part, on which the cartridge 100 for an ultrasonic medical instrument is detachably mounted, is formed in the head 21.

Meanwhile, the cartridge 100 for an ultrasonic medical instrument includes a cartridge housing 101, the first movement unit 130, a second movement unit 150, and the ultrasonic wave generating unit 211.

The cartridge housing 101 has a hollow tub shape, and is attached to the attachment part of the handpiece 10. The cartridge housing 101 includes a closed interior space while including a transparent window at a lower portion thereof. The cartridge housing 101 accommodates a medium having a low ultrasonic wave loss coefficient such that the ultrasonic waves irradiated by the ultrasonic wave generating unit 211 are not lost, and for example, the cartridge housing 101 accommodates a de-airing liquid in the closed interior space.

The ultrasonic wave generating unit 211 functions to output ultrasonic waves focused at a specific depth based on the RF signal provided by the handpiece. That is, the ultrasonic wave generating unit is coupled to the cartridge 100 for an ultrasonic medical instrument such that a terminal of the handpiece and a terminal of the cartridge contact each other, and receives the RF signal to output high-intensity focused ultrasound (HIFUs). For example, the ultrasonic wave generating unit may form ultrasonic waves at a specific focusing depth in skin as it has a specific RF value. Furthermore, the ultrasonic wave generating unit may have a semispherical shape, and may have a semi-cylindrical shape.

The ultrasonic wave generating unit 211 may be coupled to the second movable body of the second movement unit, which will be described below, and may be moved in the second axial direction as the second movable body is moved in the second axial direction, and thus, a location thereof in the second axial direction may be changed. Accordingly, the ultrasonic wave generating unit may provide ultrasonic waves while being moved in the second axial direction by the second movement unit, and may provide ultrasonic waves after being moved to a preset location by the second movement unit.

Meanwhile, when the ultrasonic wave generating unit is moved while being coupled to the second movable body, the ultrasonic wave generating unit includes a through-hole at a center thereof, and a movement shaft of the second movement unit may pass through the through-hole to be coupled to the second movable body.

The first movement unit 130 functions to move the ultrasonic wave generating unit in the first axial direction (that is, the X axial direction). The first movement unit 130 is accommodated in the cartridge housing 101, and is configured such that the first movable body 132 is movable in the first axial direction.

As an embodiment, the first movable body 132 may be moved in the first axial direction by the first driving unit such that a location thereof in the first axial direction is adjusted. For example, when the first driving unit is the driving actuator 31, the first movable body 132 may be connected to a rod of the driving actuator 31, and may be moved in the first axial direction as the rod of the driving actuator 31 is moved in the first axial direction. Furthermore, when the first driving unit is a motor, the first movable body 132 may be connected to a rotary screw of the motor, and may be moved in the first axial direction as the rotary screw is rotated.

Furthermore, as another embodiment, the first movement unit 130 may include the piezoelectric motor, and the piezoelectric motor may move the first movable body 132 in the first axial direction based on a current provided by the handpiece to change the location of the first movable body 132 in the first axial direction.

The second movement unit 150 functions to move the ultrasonic wave generating unit in the second axial direction (that is, a depth direction).

As an embodiment, the second movement unit 150 is coupled to one side of the first movable body, of which the location in a first axial direction is changed by the first movement unit, and is configured such that the second movable body reciprocates in the second axial direction that is perpendicular to the first axial direction. The disposition location of the second movement unit in the first axial direction in the cartridge is set according to a location movement of the first movable body.

Furthermore, as an embodiment, the second movement unit 150 may be the piezoelectric motor. The piezoelectric motor linearly moves the second movable body 152 as an RF frequency is provided thereto.

For example, the piezoelectric motor may include a piezoelectric actuator 150-1, a movement shaft 150-2 extending in the second axial direction from the piezoelectric actuator 150-1, and the second movable body 152 surrounding an outer peripheral surface of the movement shaft 150-2 and fixed due to frictions with the outer peripheral surface of the movement shaft 150-2, and the ultrasonic wave generating unit 211 may be coupled to a lower portion of the second movable body 152 (see FIGS. 1 to 3).

When vibration is applied to the movement shaft 150-2 of the piezoelectric motor due to a change of a shape (contraction or expansion) of the piezoelectric actuator 150-1 that receives the RF signal from a frequency generator, to which a voltage is applied, the second movable body 152 is moved along the movement shaft 150-2. In this way, when the second movable body 152 is moved in the second axial direction along the movement shaft 150-2, the ultrasonic wave generating unit 211 coupled to the second movable body 152 also is moved in the second axial direction. The ultrasonic wave generating unit and the piezoelectric motor may receive RF signals from individual RF modules or the same RF module to be driven, and preferably, it is preferable that the RF signals are received from the individual RF modules.

Moreover, the movement shaft 150-2 is coupled to the second movable body 152 in a state of being penetrated, and the ultrasonic wave generating unit 211 may be moved in the second axial direction as the second movable body 152 is moved in the second axial direction so that the focusing depth of ultrasonic waves (that is, high-intensity focused ultrasound) may be changed.

While the first movement unit 130 is driven under the control of the controller in the handpiece, the second movement unit 150 may be moved in the second axial direction, and the location of the second movement unit 150 in the second axial direction may be set before the first movement unit 130 is driven.

The driving unit may change the disposition location of the first movable body in the first axial direction with the first movement unit and change a location of the second movable body in the second axial direction at the same time when a treatment is performed by outputting ultrasonic waves.

The first movement unit 130 and the second movement unit 150 are controlled by the handpiece or the controller included in the handpiece. The controller may control movement of the first movable body 132 in the first axial direction by controlling the driving of the first driving unit, and may control movement of the second movable body 152 in the second axial direction by controlling the driving of the second driving unit.

As an embodiment, a target location of the ultrasonic wave generating unit 211 is set, the controller may move the ultrasonic wave generating unit 211 to the target location by at least one of moving the first movable body 132 in the first axial direction and moving the second movable body 152 in the second axial direction. As a result, the high-intensity focused ultrasound of the ultrasonic wave generating unit 211 may be provided to a target focus below a skin surface.

Thereafter, the controller may move the ultrasonic wave generating unit 211 along a linear path in the first axial direction by moving the first movable body 132 in the first axial direction. Accordingly, the high-intensity focused ultrasound of the ultrasonic wave generating unit 211 may be provided along the linear path (that is, an X axis path) in the first axial direction below the skin surface.

Furthermore, the controller may move the ultrasonic wave generating unit 211 along a linear path in the second axial direction by moving the second movable body 152 in the second axial direction. Accordingly, the high-intensity focused ultrasound of the ultrasonic wave generating unit

211 may be provided along the linear path (that is, a Z axis path) in the second axial direction below the skin surface.

Furthermore, the controller may move the ultrasonic wave generating unit 211 along a curved path by moving the first movable body 132 in the first axial direction and moving the second movable body 152 in the second axial direction at the same time. Accordingly, the high-intensity focused ultrasound of the ultrasonic wave generating unit 211 may be provided along the curved path below a skin surface.

In this way, while the ultrasonic wave generating unit 211 is moved in the linear path or the curved path, the high-intensity focused ultrasound may be output continuously or periodically.

Hereinafter, various embodiments of setting a focusing depth of ultrasonic waves in the skin by adjusting the location of the ultrasonic wave generating unit in the second axial direction (that is, the Z axial direction) will be described.

In the focused ultrasonic wave cartridge according to the embodiment of the inventive concept, the second movement unit 150 is coupled to the first movement unit 130 and is moved. For example, the piezoelectric motor of the second movement unit 150 is coupled to one side (for example, a lower surface or a side surface) of the first movable body 132 of the first movement unit 130 that is linearly moved by the power provided by the driving unit of the handpiece.

In detail, the piezoelectric motor, as illustrated in FIG. 1, may be coupled to the lower surface of the first movable body 132, and a disposition location thereof may be changed in the interior of the cartridge as the location of the first movement unit 130 is changed. That is, as the first movement unit 130 is driven by the driving unit of the handpiece, the piezoelectric motor is coupled to the first movable body 132 and is moved together as the first movable body 132 is moved. That is, the second driving unit that drives the first movable body 132 in the Z axial direction is integrally moved in a space in the cartridge with the first movable body 132 of the first movement unit 130.

The piezoelectric motor moves the ultrasonic wave generating unit coupled to a column corresponding the Z axis movement path through output of ultrasonic waves. The piezoelectric motor changes a location of a movement module, to which the ultrasonic wave generating unit is coupled, based on an intensity of the provided RF and a period of time, for which the RF is provided. For example, the piezoelectric motor may move the movement module faster when the intensity of the provided RF is increased.

Through this, because a volume of the space filled with the de-airing liquid is not changed even though the ultrasonic wave generating unit is moved in the Z axial direction in the cartridge, the cartridge may be implemented in a closed state. That is, because only the change in the location of the first movable body 132 due to the driving of the driving unit of the handpiece and the change in the location of the second movable body 152 due to the driving of the piezoelectric motor occur in a state, in which the first driving unit that causes a change in the location of the ultrasonic wave generating unit 211 in the X axial direction and the second driving unit that causes a change in the location of the ultrasonic wave generating unit 211 in the Z axial direction are included in the interior space of the cartridge, a volume of the configurations included in the cartridge is not changed during an ultrasonic wave procedure. Accordingly, the ultrasonic wave treatment apparatus according to the embodiment of the inventive concept may move the ultrasonic wave generating unit in the first axial direction and the second axial direction in a state, in which a predetermined amount of the de-airing liquid is filled in the cartridge, of which the volume of the interior is fixed.

The ultrasonic wave generating unit may be coupled to the movement module that is moved on a track by ultrasonic vibrations provided by the piezoelectric motor in various manners. As an embodiment, as illustrated in FIGS. 1 to 3, because the hole is formed at the center of the ultrasonic wave generating unit and the ultrasonic wave generating unit is directly coupled to a lower end of the Z axis movement module so that the location of the movement module is changed, the ultrasonic wave generating unit may be disposed at a specific depth corresponding to a desired focusing depth. Then, the column of the piezoelectric motor corresponding to the movement track may be disposed below the ultrasonic wave generating unit according to the disposition location of the ultrasonic wave generating unit, but the column may not cause any influence as the focusing distance of the ultrasonic waves (that is, the location of the focusing point according to the curvature of the ultrasonic wave generating unit) is set.

Furthermore, as another embodiment, the movement module of the piezoelectric motor may extend laterally so that the ultrasonic wave generating unit is disposed. Then, the location of the ultrasonic wave generating unit on the Z axis is the same as that of the movement module, but the planar location of the ultrasonic wave generating unit on the X axis becomes different. For example, the location of the ultrasonic wave generating unit may be different from the location of the movement module of the piezoelectric motor by a distance that is caused as it is coupled to a side surface of the movement module in the X axial direction or the Y axial direction.

Furthermore, as an embodiment, as the cartridge is electrically connected to the handpiece while being fastened to the handpiece, the piezoelectric motor and the ultrasonic wave generating unit coupled thereto receive RF signals, respectively. That is, the piezoelectric motor and the ultrasonic wave generating unit receive the RF signals, respectively, from the handpiece to be driven.

For example, because RF signal values that are necessary for changing the location of the ultrasonic wave generating unit 211 in the Z axial direction and RF signal values for providing high-intensity focused ultrasound to skin may be different at different time points, the piezoelectric motor may receive an RF signal from an RF generating module that is different from the ultrasonic wave generating unit that outputs ultrasonic waves to the skin. For example, the piezoelectric motor may receive a current provided by an RF circuit disposed in the handpiece, and the ultrasonic wave generating unit may receive a current from an RF circuit provided in the body of the medical instrument.

Furthermore, as illustrated in FIGS. 1 to 3, the piezoelectric element is disposed in a packaged state such that the de-airing liquid is not introduced. That is, because the location of the second movable body is changed by providing frequencies and generating vibration, only an electrical wire for control may be connected in a state, in which a vibration unit (151 of FIG. 5) of the piezoelectric module is packaged, such that the vibration unit is not influenced by the de-airing liquid filled in the cartridge.

Furthermore, as in another embodiment, the cartridge includes a movement module location measuring unit. The movement module location measuring unit measures the location of the movement module, to which the ultrasonic wave generating unit is coupled, to set an ultrasonic wave focusing depth in the skin. That is, the movement module location measuring unit functions to determine whether the second movable body is disposed at a location in the second axial direction, at which a desired focusing depth may be formed.

In particular, when the second movement unit is a piezoelectric motor and the piezoelectric motor is continuously driven to change to the location of the ultrasonic wave generating unit 211 in the second axial direction, the element characteristics of the piezoelectric motor are changed, and a movement distance of the ultrasonic wave generating unit 211 in the second axial direction may vary when the same RF signal is provided. Accordingly, a movement module location measuring unit measuring a location of the second movable body in the second axial direction to accurately set a focusing depth without being influenced by the deformation in the characteristics of the piezoelectric motor is required.

The movement module location measuring unit may be implemented in various manners. In an embodiment, the movement module location measuring unit, as illustrated in FIG. 3, is a track 154, in which a plurality of Hall sensors 155 are disposed on a side surface of the piezoelectric motor at a specific interval. Because a magnet (not illustrated) is provided on a side surface of the movement module (that is, the second movable body) or the ultrasonic wave generating unit 211, a location of the ultrasonic wave generating unit 211 in the depth direction may be determined based on the Hall sensor 155 that is influenced by the magnet when the second movable body 152 is moved in the Z axial direction. In detail, when the location of the ultrasonic wave generating unit 211 in the Z axial direction is changed through the driving of the piezoelectric motor, the controller of the body or the handpiece may determine the location of, among the plurality of Hall sensors, the Hall sensor 155 that senses magnetism (or a magnetic field) of a magnet (not illustrated) coupled to the ultrasonic wave generating unit 211 as the location of the ultrasonic wave generating unit 211 in the Z axial direction (that is, the second axial direction).

As an embodiment, as in FIG. 3, as the track 154, in which the Hall sensor 155 is disposed, is also moved when the ultrasonic wave generating unit 211 is moved in the X axial direction (that is, the first axial direction) by the first movable body 132, the location thereof may be measured regardless of the location of the ultrasonic wave generating unit 211 in the X axial direction. Then, a structure, in which the internal components of the cartridge housing 101 are not influenced when the Hall sensor track is moved together with the piezoelectric motor in the X axial direction, may be formed. In detail, the track is coupled to one side of the first movable body to be disposed to be parallel to the movement shaft of the second movement unit, and may be moved integrally with the second movement unit when the second movement unit is moved in the first axial direction by the first movable body.

Furthermore, as another example, when the ultrasonic wave generating unit 211 is moved into the same depth after the location of the ultrasonic wave generating unit 211 in the Z axial direction is set at opposite ends of the cartridge 100 during treatment, the track 154 provided with the Hall sensor 155 may be provided on one side surface of the cartridge 100 for initial setting of the depth at the start of treatment. In detail, the track may be disposed on one side surface of the interior of the cartridge, and the controller may set the disposition location of the first movable body in the second axial direction after moving the first movable body to the one side of the cartridge, on which the track is disposed, before starting an ultrasonic wave treatment.

Furthermore, as another embodiment, the movement module location measuring unit may include a third movable body moving between the second movable body and a Z axis driving unit by a short distance, separately from the second movable body, to which the ultrasonic wave generating unit is coupled. That is, the third movable body may be moved by a distance obtained by downscaling the movement distance of the second movable body at a specific ratio, and may calculate the location of the second movable body based on a location of the third movable body.

Furthermore, as another embodiment, the movement module location measuring unit may be an infrared ray emitting unit and an infrared ray receiving unit. For example, the movement module may include an infrared ray emitting unit, and a plurality of light receiving units may be disposed on a side surface of the cartridge housing at a specific interval to measure whether the movement module reaches a desired depth.

Furthermore, as another embodiment, the movement module location measuring unit may be an ultrasonic wave distance measuring module 153. The ultrasonic wave distance measuring module measures a distance from the driving unit of the piezoelectric motor to the ultrasonic wave generating unit. The ultrasonic wave distance measuring module 153, as in FIG. 2, is provided in a piezoelectric motor package, and outputs ultrasonic waves for measuring a distance to the ultrasonic wave generating unit 211. Then, the ultrasonic wave distance measuring module 153 may output ultrasonic waves for measuring the distance to the ultrasonic wave generating unit in parallel to the movement shaft of the second movable body, and may accurately measure a linear distance in the second axial direction.

Through this, the ultrasonic wave distance measuring module 153 may measure the location of the ultrasonic wave generating unit 211 in the Z axial direction based on the ultrasonic waves that returns after being reflected by the ultrasonic wave generating unit 211. Through this, even when the characteristics of the piezoelectric motor deformation as the piezoelectric motor is used, the location of the ultrasonic wave generating unit 211 in the Z axial direction may be accurately calculated.

Furthermore, as an embodiment, the controller of the handpiece may determine deformation characteristics of the piezoelectric motor. Because the deformation characteristics of the piezoelectric motor may be changed as the ultrasonic wave output module is used, a distance, by which the movement module of the piezoelectric motor is moved, may vary when the same RF signal is provided. Accordingly, it is necessary to determine the deformation characteristics for accurately setting the depth of the ultrasonic wave generating unit 211 in the Z axial direction, and based on this, provide an RF signal for controlling the movement module. For example, the controller may determine and set the changed characteristics based on a period of time, for which an RF signal of a specific value arrives when the RF signal is provided from an initial point to a final point. The controller may set an RF signal provision condition for setting a depth based on the corresponding time value.

Figure 6:
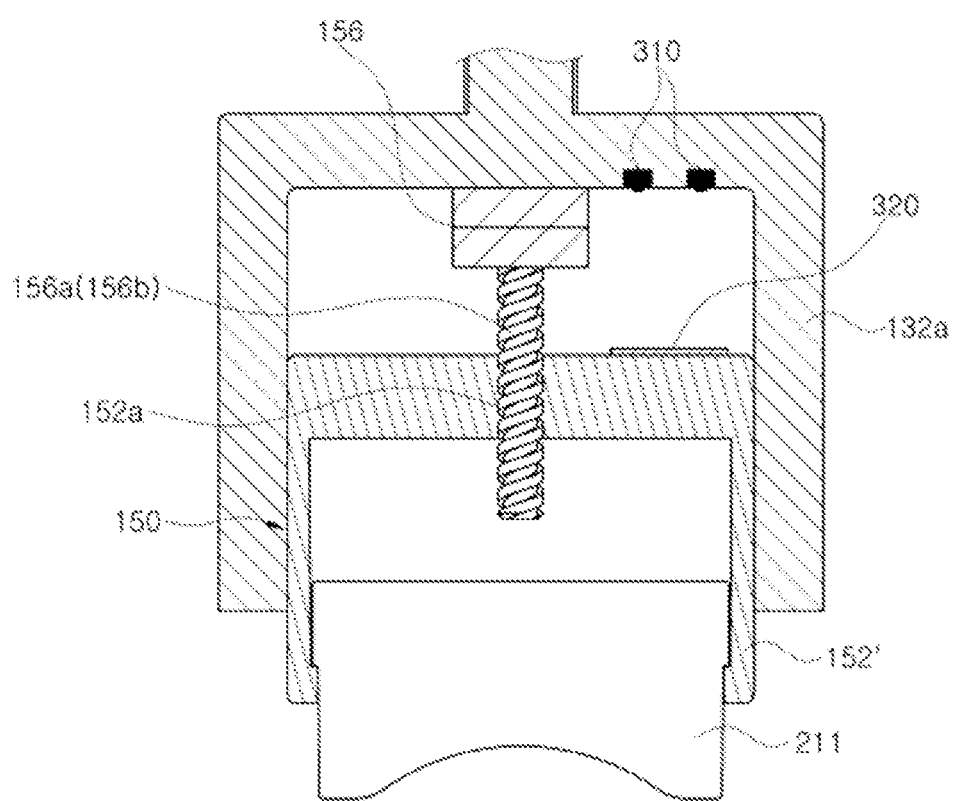
FIG. 6 is a cross-sectional view of a cartridge for an ultrasonic medical instrument according to an embodiment of the inventive concept.

FIG. 6 is a cross-sectional view of a cartridge for an ultrasonic medical instrument according to an embodiment of the inventive concept.

Figure 7A:
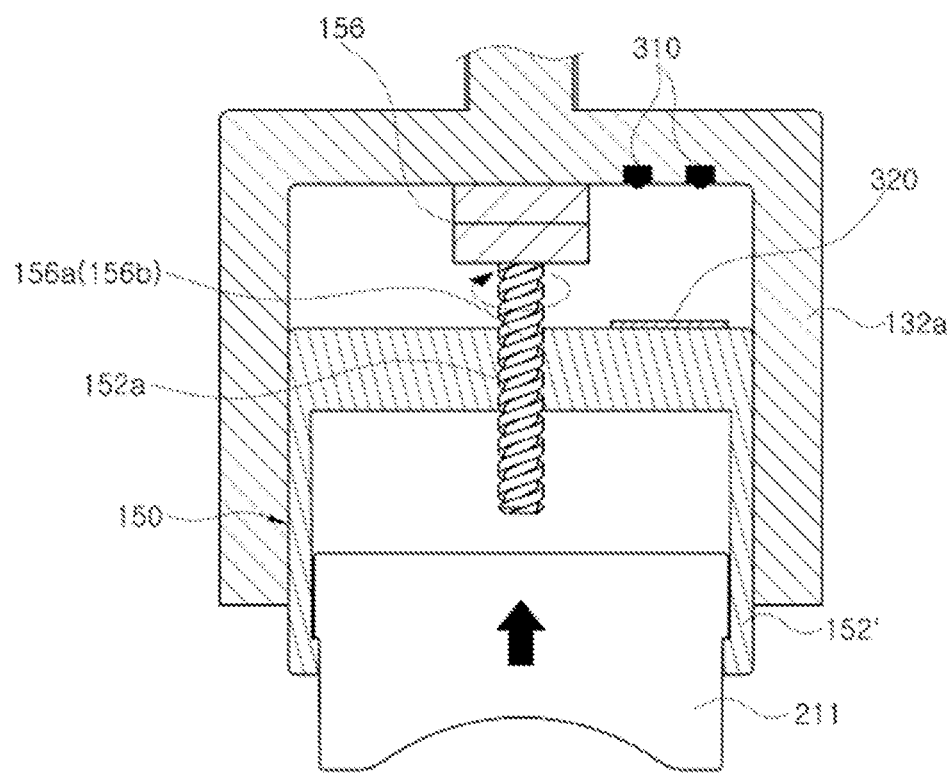
FIGS. 7A and 7B are cross-sectional views illustrating a movement state of an ultrasonic wave generating unit of a cartridge for an ultrasonic medical instrument in a second axial direction according to an embodiment of the inventive concept.
Figure 7B:
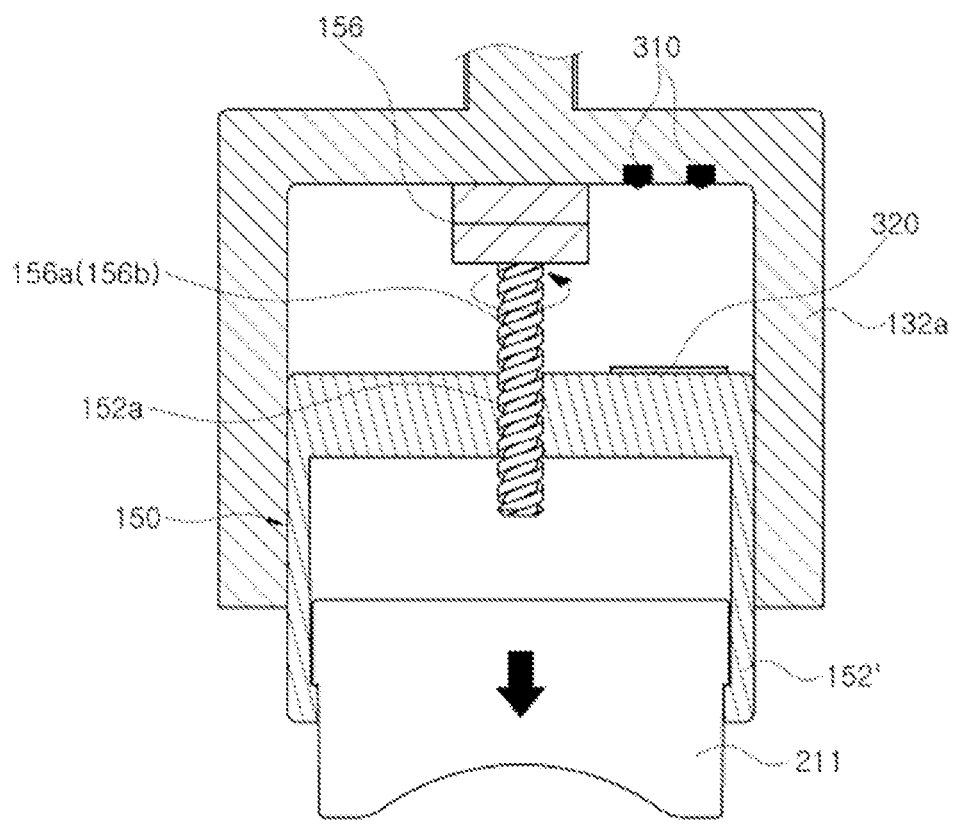

FIGS. 7A and 7B are cross-sectional views illustrating a movement state of an ultrasonic wave generating unit of a cartridge for an ultrasonic medical instrument in a second axial direction according to an embodiment of the inventive concept.

Figure 8:
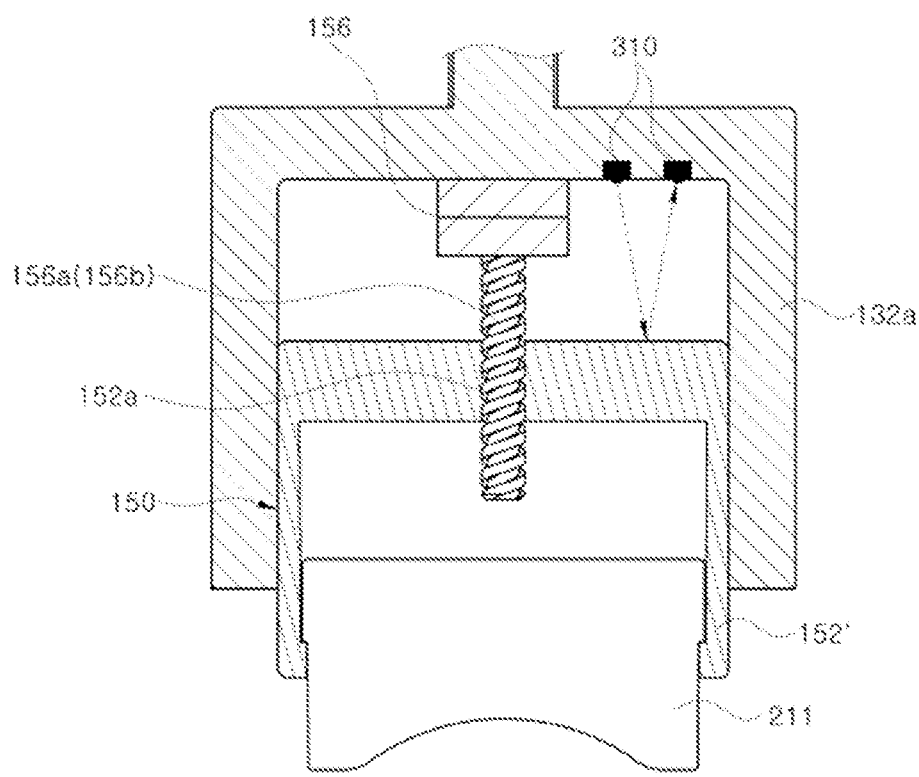
FIGS. 8 and 9 are cross-sectional views illustrating a state of detecting a location of an ultrasonic wave generating unit in a second axial direction by an ultrasonic wave generating unit location measuring unit of a cartridge for an ultrasonic medical instrument according to an embodiment of the inventive concept.
Figure 9:
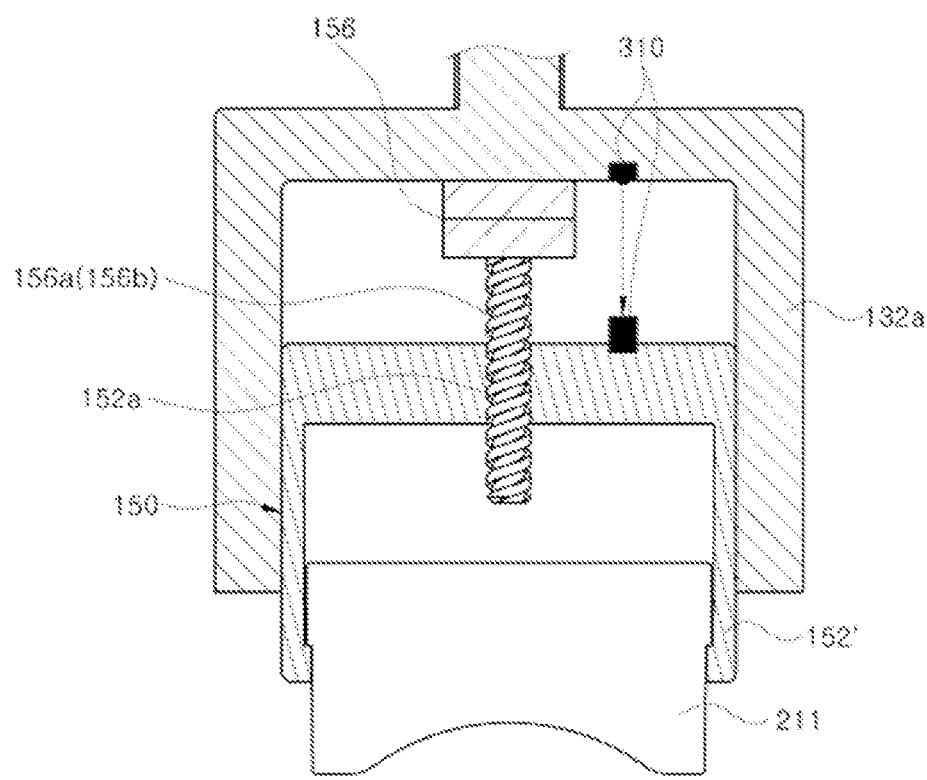

FIGS. 8 and 9 are cross-sectional views illustrating a state of detecting a location of an ultrasonic wave generating unit in a second axial direction by an ultrasonic wave generating unit location measuring unit of a cartridge for an ultrasonic medical instrument according to an embodiment of the inventive concept.

Referring to FIG. 6, in the present embodiment, the second movement unit 150 may include a piezoelectric rotary motor 156 coupled to the first movable body 132, the piezoelectric rotary motor 156 may have a driving shaft 156a disposed in the second axial direction, the second movable body 152' may be installed to reciprocate in the second axial direction through rotation of the driving shaft 156a, and the ultrasonic wave generating unit 211 may be coupled to a second movable body 152'.

In the present embodiment, the piezoelectric rotary motor 156 may be coupled to the first movable body 132, and a piezoelectric material may be embedded therein. A shape of the piezoelectric material is finely changed by the RF signal provided by the RF generating module, and the piezoelectric rotary motor 156 may finely rotate the driving shaft 156a through the fine change of the shape of the piezoelectric material.

In this way, as the driving shaft 156a is finely rotated, the locations of the second movable body 152' and the ultrasonic wave generating unit 211, which are moved in the second axial direction through rotation of the driving shaft 156a, may be precisely changed. As a result, a focusing depth of the high-intensity focused ultrasound of the ultrasonic wave generating unit 211, which is changed according to the location of the ultrasonic wave generating unit 211 in the second axial direction, may be precisely changed.

As an example, the piezoelectric rotary motor 156 may change movement speeds of the second movable body 152' and the ultrasonic wave generating unit 211 in the second axial direction based on the intensity of the RF signal provided by the RF generating module. For example, as the intensity of the RF signal provided to the piezoelectric rotary motor 156 increases, the rotational speed of the driving shaft 156a increases, and thus, the movement speeds of the second movable body and the ultrasonic wave generating unit 211 in the second axial direction also increase. To the contrary, as the intensity of the RF signal provided to the piezoelectric rotary motor 156 decreases, the rotational speed of the driving shaft 156a decreases, and thus, the movement speeds of the second movable body 152' and the ultrasonic wave generating unit 211 in the second axial direction also decrease.

As another example, the piezoelectric rotary motor 156 may change the movement distance of the ultrasonic wave generating unit 211 in the second axial direction based on a period of time, for which the RF signal is provided by the RF generating module. For example, as the period of time, for which the RF signal provided to the piezoelectric rotary motor 156, increases, the period of rotation of the driving shaft 156a increases, and thus, the movement distances of the ultrasonic wave generating unit 211 in the second axial direction also increases. To the contrary, as the period of time, for which the RF signal provided to the piezoelectric rotary motor 156, decreases, the period of rotation of the driving shaft 156a decreases, and thus, the movement distances of the ultrasonic wave generating unit 211 in the second axial direction also decreases.

The intensity of the RF signal provided to the above-described piezoelectric rotary motor 156 and the period of time, for which the RF signal is provided to the piezoelectric rotary motor 156, may be controlled by the controller.

The driving shaft 156a is disposed to protrude from the piezoelectric rotary motor 156 in the second axial direction, and a spiral screw 156b is formed at an outer circumference of the driving shaft 156a in the second axial direction. A screw hole 152a of the second movable body 152', which will be described below, is screw-coupled to the screw 156b. Furthermore, the second movable body 152' may be supported by a guide unit 132a of the first movable body 132, which will be described below to be prevented from being rotated.

Accordingly, as the screw hole 152a of the second movable body 152' is moved along the screw 156b of the driving shaft 156a in the second axial direction when the driving shaft 156a is rotated, the location of the second movable body 152' in the second axial direction may be changed.

In this way, when the location of the second movable body 152' in the second axial direction is changed, the location of the ultrasonic wave generating unit 211 coupled to the second movable body 152' in the second axial direction may also be changed, and accordingly, the focusing depth of the high-intensity focused ultrasound of the ultrasonic wave generating unit 211 may also be changed.

As an example, referring to FIGS. 7A and 7B, the screw 156b of the driving shaft 156a may have a right-handed screw shape. In this way, when the screw 156b has a right-handed screw shape, the second movable body 152' may be raised along the screw 156b having the right-handed screw shape when the driving shaft 156a is rotated in a clockwise direction with reference to FIG. 7A, and the second movable body 152' may be lowered along the screw 156b having the right-handed screw shape when the driving shaft 156a is rotated in a counterclockwise direction.

As another example, the screw 156b of the driving shaft 156a may have a left-handed screw shape. In this way, when the screw 156b has a left-handed screw shape, the second movable body 152' may be lowered along the screw 156b having the left-handed screw shape when the driving shaft 156a is rotated in a clockwise direction, and the second movable body 152' may be raised along the screw having the left-handed screw shape when the driving shaft 156a is rotated in a counterclockwise direction.

The cartridge for an ultrasonic medical instrument according to the embodiment may maintain a state, in which the second movable body 152' is screw-coupled to the driving shaft 156a when the second movable body 152' is moved in the second axial direction or stopped, and thus the second movable body 152' may be prevented from being influenced by the gravitational force and being deflected.

In the present embodiment, the second movable body 152' may be inserted into an interior of the guide unit 132a, which will be described below, to reciprocate along the second axial direction, and the screw hole 152a screw-coupled to the screw 156b of the driving shaft 156a is formed in a central axis of the second movable body 152'.

The screw hole 152a has a diameter corresponding to the driving shaft 156a, and a spiral screw thread corresponding to the screw 156b is formed on an inner peripheral surface of the screw hole 152a.

The first movable body 132, as described above, has the guide unit 132a that supports the second movable body 152' to prevent rotation of the second movable body 152'.

The guide unit 132a may be formed at a lower portion of the first movable body 132. The guide unit 132a may have a shape, a lower portion of which is opened, and the second movable body 152' may be inserted into the interior of the guide unit to reciprocate along the second axial direction.

The guide unit 132*a* has a circumferential surface corresponding to an outer circumference of the second movable body 152', and may function to support the outer circumference of the second movable body 152' through the circumferential surface to prevent rotation of the second movable body 152' and guide movement of the second movable body 152' in the second axial direction.

A communication hole (not illustrated) that communicates a gap between the guide unit 132*a* and the second movable body 152' and the interior of the cartridge housing 101 may be formed in the guide unit 132*a*.

The communication hole functions as a passage, through which the de-airing liquid filled in the interior of the cartridge housing 101 fills the gap between the guide unit 132*a* and the second movable body 152'.

The de-airing liquid filled in the gap between the guide unit 132*a* and the second movable body 152' through the communication hole may be filled or discharged as the ultrasonic wave generating unit 211 is moved in the second axial direction as the second movable body 152' is moved in the second axial direction, but the filling and discharging of the de-airing liquid in and from the gap does not cause a change in a whole internal volume of the cartridge 100 for an ultrasonic medical instrument.

Accordingly, in the present embodiment, because the whole internal volume of the cartridge 100 for an ultrasonic medical instrument is not changed even when the location of the ultrasonic wave generating unit 211 in the second axial direction is adjusted, the structure of the cartridge 100 for an ultrasonic medical instrument may be simplified and may be simply manufactured.

Meanwhile, as the piezoelectric material of the piezoelectric rotary motor 156 is easily deformed by the RF signal, the rotational speed of the driving shaft 156*a* may vary even when the same RF signal is provided, and accordingly, the location of the ultrasonic wave generating unit 211 in the second axial direction may deviate from a preset location. Accordingly, in order to accurately set the location of the ultrasonic wave generating unit 211 in the second axial direction even without being influenced by the deformation characteristics of the piezoelectric material, an ultrasonic wave generating unit location measuring unit 310 that detects the location of the ultrasonic wave generating unit 211 in the second axial direction is necessary.

To achieve this, the cartridge 100 for an ultrasonic medical instrument according to the embodiment of the inventive concept may include the ultrasonic wave generating unit location measuring unit 310. In the present embodiment, the ultrasonic wave generating unit location measuring unit 310 functions to detect the location of the ultrasonic wave generating unit 211 in the second axial direction.

The ultrasonic wave generating unit location measuring unit 310 is installed to be spaced apart from the second movable body 152' in the second axial direction, and for example, may be installed on a ceiling surface of the interior of the guide unit 132*a*. In this way, when the ultrasonic wave generating unit location measuring unit 310 is installed on the ceiling surface of the interior of the guide unit 132*a*, an interference between the second movable body 152' and the ultrasonic wave generating unit location measuring unit 310 may be prevented when the second movable body 152' is moved in the second axial direction.

The ultrasonic wave generating unit location measuring unit 310 may measure a relative distance to the second movable body 152' with respect to the second axial direction by outputting sensing light to the second movable body 152' in the second axial direction and sensing reflected light that is reflected by the second movable body 152', and may calculate the location of the ultrasonic wave generating unit 211 in the second axial direction by adding a distance value from points of the second movable body 152', to which the sensing light is input, to a lower end of the ultrasonic wave generating unit 211 in the second axial direction, for the measured distance value.

For example, referring to FIG. 8, the light emitting unit and the light receiving unit of the ultrasonic wave generating unit location measuring unit 310 may be disposed in parallel to the ceiling surface of the guide unit 132*a*. The light emitting unit may emit the sensing light to an upper surface of the second movable body 152' in the second axial direction, and the light receiving unit may receive the reflected light that is reflected on an upper surface of the second movable body 152'.

Furthermore, referring to FIG. 9, the light emitting unit of the ultrasonic wave generating unit location measuring unit 310 may be disposed on the ceiling surface of the guide unit 132*a*, and the light receiving unit of the ultrasonic wave generating unit location measuring unit 310 may be disposed on the upper surface of the second movable body 152'. The light emitting unit may emit the sensing light to the light receiving unit in the second axial direction, and the light receiving unit may receive the sensing light output from the light emitting unit.

Moreover, the ultrasonic wave generating unit location measuring unit 310 may measure a relative distance to the second movable body 152' by sensing an intensity of the reflected light, which is changed according to the relative distance to the second movable body 152'. In particular, the ultrasonic wave generating unit location measuring unit 310 may convert the reflected light into a voltage signal, and may measure the relative distance to the second movable body 152' through a difference between the levels of the voltage signals that are changed according to the intensities of the reflected light.

As another example, the ultrasonic wave generating unit location measuring unit 310 may measure the relative distance to the second movable body 152' through a difference between an output time of the sensing light and a sensing time of the reflected light.

The sensing light output from the ultrasonic wave generating unit location measuring unit 310 may include at least one of an infrared ray, a laser beam, an ultraviolet ray, and an LED light, and the ultrasonic wave generating unit location measuring unit 310 may include at least one of an infrared sensor, a laser sensor, an ultraviolet sensor, and a light sensor that senses the sensing light, but is not specifically limited thereto.

Meanwhile, as the intensity of the reflected light that is reflected by the second movable body 152' becomes very weak when the relative distance from the ultrasonic wave generating unit location measuring unit 310 to the second movable body 152' becomes larger to a specific level, the ultrasonic wave generating unit location measuring unit 310 may not sense the reflected light.

In order to prevent this, a reflection plate (not illustrated) for improving the reflectivity of the sensing light may be installed at a point of the second movable body 152', at which the sensing light is input.

The reflection plate (not illustrated) may be disposed in parallel to the ultrasonic wave generating unit location measuring unit 310 to reflect the sensing light input from the ultrasonic wave generating unit location measuring unit 310 perpendicularly.

As an example, the reflection plate (not illustrated) may be a glass bead, a mirror, or the like for improving the reflectivity of the sensing light, but is not specifically limited thereto.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A cartridge for an ultrasonic medical device, the cartridge comprising:
    a cartridge housing configured to be detachably mounted on a handpiece;
    a first movable body accommodated in the cartridge housing, wherein the first movable body is configured to reciprocate in a first axial direction;
    a second movable body accommodated in the cartridge housing, wherein the second movable body is coupled to the first movable body and is configured to reciprocate in a second axial direction that is perpendicular to the first axial direction;
    an ultrasonic wave generator coupled to the second movable body, wherein the ultrasonic wave generator is configured to generate focused ultrasound having a focusing distance; and
    a piezoelectric motor coupled to the first movable body and configured to be driven based on an electrical signal by a power source, wherein the piezoelectric motor is configured to reciprocate the second movable body in the second axial direction, wherein the piezoelectric motor has a driving shaft disposed along the second axial direction, and wherein the driving shaft of the piezoelectric motor is configured to rotate to reciprocate the second movable body in the second axial direction;
    wherein the reciprocation of the first movable body in the first axial direction sets a location of the second movable body in the first axial direction; and
    wherein the handpiece is connected to or comprises a controller configured to control movement of the first and second movable bodies.

2. The cartridge of claim 1, wherein the first movable body is coupled to the handpiece, and is configured to be actuated in the first axial by the handpiece.

3. The cartridge of claim 2, wherein the first and second movable bodies are configured to be simultaneously actuated in the first and second axial directions, respectively, by the handpiece.

4. The cartridge of claim 1, wherein the electrical signal is a radiofrequency (RF) signal.

5. The cartridge of claim 1, further comprising:
    a sensor configured to determine a location of the ultrasonic wave generator in the second axial direction.

6. The cartridge of claim 5,
    wherein determining the location of the ultrasonic wave generator is based on measuring a distance to the ultrasonic wave generator in the second axial direction.

7. The cartridge of claim 6,
    wherein measuring the distance is based on outputting sensing light to the second movable body and detecting the sensing light at a location on the second movable body.

8. The cartridge of claim 1, wherein the second movable body includes a through-hole at a center thereof,
    wherein the through-hole accommodates a movement shaft passing through the through-hole.

9. The cartridge of claim 1, wherein the piezoelectric motor is a piezoelectric rotary motor.

10. The cartridge of claim 9, wherein the first movable body has a guide that supports the second movable body to prevent rotation of the second movable body;
    wherein a spiral screw is formed in the driving shaft in the second axial direction; and
    wherein a screw hole screw-coupled to the screw is formed in the second movable body.

11. The cartridge of claim 9, further comprising:
    a sensor configured to detect a location of the ultrasonic wave generator in the second axial direction.

12. The cartridge of claim 11, wherein determining the location of the ultrasonic wave generator is based on measuring a distance to the ultrasonic wave generator in the second axial direction; and
    wherein measuring the distance is based on outputting sensing light to the second movable body and detecting the sensing light at a location on the second movable body.

13. The cartridge of claim 12, further comprising:
    a reflection plate configured to improve reflectivity of the sensing light at a point, at which the sensing light is input to the second movable body.

14. An ultrasonic medical device, comprising:
    a handpiece; and
    a cartridge detachably mountable on the handpiece, the cartridge comprising:
        a first movable body configured to reciprocate in a first axial direction;
        a second movable body coupled to the first movable body and configured to reciprocate in a second axial direction that is perpendicular to the first axial direction;
        an ultrasonic wave generator coupled to the second movable body, wherein the ultrasonic wave generator is configured to generate ultrasound; and
        a piezoelectric motor coupled to the first movable body and configured to be driven based on an electrical signal by a power source, wherein the piezoelectric motor is configured to reciprocate the second movable body in the second axial direction, wherein the piezoelectric motor has a driving shaft disposed along the second axial direction, and wherein the driving shaft of the piezoelectric motor is configured to rotate to reciprocate the second movable body in the second axial direction;
    wherein the reciprocation of the first movable body in the first axial direction sets a location of the second movable body in the first axial direction; and
    wherein the handpiece is connected to or comprises a controller configured to control movement of the first and second movable bodies.

15. The device of claim 14, wherein the first movable body is coupled to the handpiece, and wherein the handpiece is configured to actuate the first movable body in the first axial direction.

16. The device of claim 14, wherein the handpiece is configured to simultaneously actuate the first and second movable bodies in the first and second axial directions, respectively.

17. The device of claim 14, wherein the electrical signal is a radiofrequency (RF) signal.

18. The device of claim 14, further comprising:
a sensor configured to determine a location of the ultrasonic wave generator in the second axial direction.

19. The device of claim 14, wherein the second movable body includes a through-hole at a center thereof, wherein the through-hole accommodates a movement shaft passing through the through-hole.

20. An ultrasonic medical device, comprising:
a controller,
a handpiece connected to the controller, and
a cartridge detachably mountable on the handpiece, the cartridge comprising:
  a first movable body configured to reciprocate in a first axial direction;
  a second movable body coupled to the first movable body and configured to reciprocate in a second axial direction that is perpendicular to the first axial direction;
  an ultrasonic wave generator coupled to the second movable body, wherein the ultrasonic wave generator is configured to generate ultrasound; and
  a piezoelectric motor coupled to the first movable body and configured to be driven based on an electrical signal by a power source, wherein the piezoelectric motor is configured to reciprocate the second movable body in the second axial direction, wherein the piezoelectric motor has a driving shaft disposed along the second axial direction, and wherein the driving shaft of the piezoelectric motor is configured to rotate to reciprocate the second movable body in the second axial direction;
wherein the reciprocation of the first movable body in the first axial direction sets a location of the second movable body in the first axial direction; and
wherein the controller is configured to control movement of the first and second movable bodies.

* * * * *